United States Patent [19]

Peter et al.

[11] Patent Number: 4,581,166

[45] Date of Patent: Apr. 8, 1986

[54] METHOD FOR ISOLATING AND PURIFYING ANTIBIOTICS

[75] Inventors: Siegfried Peter, Uttenreuth; Hubert Coenen; Rainer Hagen, both of Essen, all of Fed. Rep. of Germany

[73] Assignee: Fried. Krupp Gesellschaft mit beschränkter Haftung, Essen, Fed. Rep. of Germany

[21] Appl. No.: 609,204

[22] Filed: May 11, 1984

[30] Foreign Application Priority Data

May 19, 1983 [DE] Fed. Rep. of Germany ....... 3318194

[51] Int. Cl.$^4$ ...................... C07K 1/14; C07D 499/18; C07D 501/12; C07D 307/94; C07H 15/22; C07C 67/58
[52] U.S. Cl. ........................... 260/112.5 R; 260/239.1; 260/351.6; 536/14; 536/16.9; 536/22; 544/20; 549/345; 549/349; 560/188
[58] Field of Search .......... 260/239.1, 351.6, 112.5 R; 544/20; 203/49; 549/345; 560/188; 435/43, 47, 64, 68, 74; 536/16.9, 22, 14

[56] References Cited

U.S. PATENT DOCUMENTS 3,969,196  7/1976  Zosel ..................................... 203/49
4,089,891  5/1978  Knauseder et al. ................. 560/188
4,354,971  10/1982  Edmundowicz et al. ....... 260/239.1

FOREIGN PATENT DOCUMENTS 3133032  3/1983  Fed. Rep. of Germany .
1439587  4/1966  France .
1462217  12/1966  France .
1341921  12/1973  United Kingdom .

Primary Examiner—Natalie Trousof
Assistant Examiner—Vera C. Clarke
Attorney, Agent, or Firm—Spencer & Frank

[57] ABSTRACT

A process is proposed for the isolation and purification of antibiotics wherein an antibiotic containing solution is extracted with an extraction agent at a temperature of from 0° to 40° C. and at a pressure which lies between the critical pressure and the ten-fold value of the critical pressure of the extraction agent, with the weight ratio of antibiotic containing solution to the extraction agent being 1:5 to 1:20, wherein the antibiotics are precipitated from the antibiotic containing extraction agent by reducing its density and wherein the extraction agent is recirculated. An entrainer may be added to the extraction agent. The reduction in density of the antibiotic containing extraction agent may be effected by expansion to a pressure of from 30 to 70 bar.

7 Claims, 1 Drawing Figure

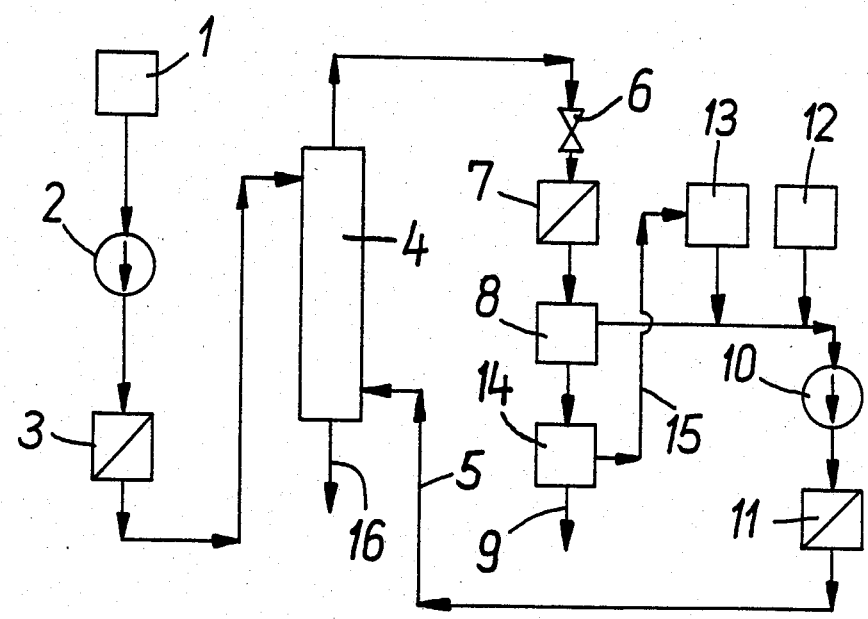

METHOD FOR ISOLATING AND PURIFYING ANTIBIOTICS

BACKGROUND OF THE INVENTION

The present invention relates to a method for isolating and purifying antibiotics. Antibiotics are a group of medicinal substances that are suitable for fighting infectious diseases. Antibiotics are usually produced by a microorganism and are capable of inhibiting or killing the growth of other microorganisms. Included in the antibiotics group are penicillins, cephalosporins, tetracyclines, aminoglucoside antibiotics, nucleoside antibiotics, macrolide antibiotics, ansamycines, peptide antibiotics and antibiotics having unique structures. By far, most antibiotics are formed in fermentation processes under sterile conditions by microorganisms which are cultivated in aerated nutrient solutions. When a culture has reached a sufficiently high content of antibiotics formed by the microorganisms, it is harvested, typically by drying, particularly spray drying, the entire culture. Alternatively, the culture may be harvested by filtration and subsequent processing of the antibiotic containing culture solution or the antibiotic containing mycelium by multiple-stage isolation and purification processes, wherein in a first stage extraction takes place and in a second stage precipitation of the extracted antibiotics occurs. It is also possible to directly precipitate the antibiotics in the first process stage from the filtered out antibiotic containing culture solution. The intermediate products obtained by precipitation must be purified, which is done, in particular, by repeated recrystallization and reprecipitation. Since for various reasons many antibiotics quickly decompose when in the dissolved state, their isolation and purification must be effected as quickly as possible. Moreover, care must be taken when isolating and purifying antibiotics to be sure that they are not overheated as most of these compounds decompose at higher temperatures.

In the known processes used for isolating and purifying antibiotics, antibiotic solutions are obtained in the individual process stages, which contain organic solvents in addition to water. Not only the antibiotics but also the organic solvents must be removed from these solutions before they can be discharged into the waste water of the manufacturing faciity. Moreover, the multiple stages of the isolating and purifying processes result in yield losses and operating malfunctions.

U.S. Pat. No. 3,969,196 to Zosel discloses a process for separating mixtures of liquid or solid substances in which the mixture is treated with a gas that is under supercritical conditions with respect to temperature and pressure, wherein the temperature range of the gas is up to more than 100° C. above its critical temperature. After separating the charged supercritical gas phase, the compounds contained therein are recovered by expansion or by an increase in the temperature of the gas. However, this reference would not lead one skilled in the art to arrive at the process of the present invention because it does not provide any indication that antibiotics can be extracted, as it relates to the extraction of simpler organic compounds. Moreover, it does not teach the possibility of conducting a separation with an extraction agent whose critical temperature lies in the range from 0° to 160° C. at a temperature which may be below the critical temperature, that is, from 0° to 40° C., and at a pressure which lies between the critical pressure and the ten-fold value of the critical pressure of the extraction agent. Nor does it teach the precipitation of the antibiotics at a temperature from 0° to 40° C. Furthermore, this reference does teach that separation processes involving organics, even if confined to gases under supercritical conditions, are not predictable as they depend on the specific constitution of the particular compound. Testing a small sample is recommended in order to ascertain the probability of success. Surprisingly, we have found that antibiotics can be separated from culture solutions as a general practice using gases under pressure which are not necessarily in the supercritical state.

SUMMARY OF THE INVENTION

It is the object of the present invention to provide a process for isolating and purifying antibiotics which significantly reduces the number of process steps required and increases the antibiotic yield.

This object is accomplished according to the present invention by extracting antibiotics from solution with an extraction agent, whose critical temperature lies in the range from 0° to 160° C., at a temperature from 0° to 40° C. and at a pressure between the critical pressure and the ten-fold value of the critical pressure of the extraction agent, with the weight ratio of the antibiotic containing solution to the extraction agent being from 1:5 to 1:20. Thereafter, the antibiotic containing extraction agent is separated from the extracted solution, the antibiotics are precipitated from the antibiotic containing extraction agent by reducing its density, and the extraction agent is returned to the extraction stage.

This process operates in an advantageous manner at temperatures which do not cause the antibiotics to decompose. Moreover, the process furnishes very pure antibiotics so that repeated recrystallization or reprecipitation can be omitted. Finally, the antibiotics are precipitated from the antibiotic containing extraction agent by reducing its density, which has the advantage of not requiring additional precipitation agents.

BRIEF DESCRIPTION OF THE DRAWING

The FIGURE shows the basic structure of the process according to the present invention in the form of a process flow diagram.

DESCRIPTION OF THE PREFERRED EMBODIMENTS

According to the present invention, the extraction agent may be $CO_2$, $C_2H_4$, $C_2H_6$, $C_3H_6$, $C_3H_8$, $C_4H_{10}$, $SF_6$, $CF_3Cl$, $CHClF_2$, $CH_3Cl$, $CF_3Br$, $C_2F_2Cl_2H_2$, $N_2O$, or a mixture of at least two of these substances. These extraction agents have the advantage that they can be removed without residue from the solution to be extracted, or they may remain in the extracted solvent, as in the case of carbon dioxide. Any of these extraction agents may be used in accordance with the invention to extract antibiotics at temperatures below their critical temperature. In the case of $C_3H_6$, $C_3H_8$, $C_4H_{10}$, $SF_6$, $C_2F_2Cl_2H_2$, $CHClF_2$, $CH_3Cl$, or $CF_3Br$, the extraction agent would necessarily be below its critical temperature during the process.

It is further provided according to the present invention that 1 to 50 weight percent ethanol, methyl acetate, ethyl acetate, propyl acetate, butyl acetate, diethyl ether, acetone, methylene chloride and/or water may be added to the extraction agent as entrainers. By using an entrainer the solubility of the extraction agent for the antibiotic to be extracted in the extraction agent can be increased in such a manner that a substantial reduction in extraction time is realized. The entrainers must be recovered from the extracted solution as well as from the extract.

According to the present invention, it is particularly advantageous if the density of the extraction agent containing antibiotics is reduced by expansion to a pressure of from 30 to 70 bar at a temperature of from 0° to 40° C., because in this temperature range antibiotics will not decompose. In some cases it may be of particular advantage to effect the expansion of the extraction agent containing antibiotics in several stages, since with this type of process sequence several antibiotic fractions of different purity can be obtained, of which those with the lower degree of purity must be recirculated.

The entrainer is recovered from the extracted solution and from antibiotic products by evaporating under reduced pressure.

The following antibiotics were testing materials for the process

Penicillin G $C_{16}H_{18}N_2O_4S$: Molecular weight 334.4 g/mol;

Penicillin V $C_{16}H_{18}N_2O_5S$; Molecular weight 350.4 g/mol;

Griseofulvin $C_{17}H_{17}ClO_6$: Molecular weight 352.8 g/mol;

Pleuromulin $C_{22}H_{34}O_5$: Molecular weight 378.5 g/mol;

Cephalosporin $C_{16}H_{20}N_3NaO_8S.2H_2O$: Molecular weight 473.4 g/mol.

The present invention will now be described in greater detail with the aid of the figure and with several examples, according to the present invention which should be adapted to the special requirements of each particular case.

The unpurified antibiotic containing solution flows from reservoir tank 1 into a pump 2 where it is compressed to the extraction pressure and conveyed into heat exchanger 3 where it is brought to the extraction temperature. The solution is then conveyed into the head section of high pressure extraction column 4, which receives the extraction agent at its foot through conduit 5. In high pressure column 4, which contains inserts to enhance the exchange of substances, the antibiotic containing solution is continuously extracted by the countercurrently flowing extraction agent, with the impurities remaining in the solution. The inserts of column 4 are for example tower packing, sieve tray, bubble cup tray and valve tray.

The antibiotic containing extraction agent is removed at the head of high pressure column 4 and is conveyed, through expansion valve 6 and heat exchanger 7, into separator 8 where the antibiotics are precipitated. If the extraction agent contains an entrainer, part of the entrainer is precipitated together with the antibiotics, and the antibiotics are separated from the entrainer in the subsequently connected separating stage 14. In this case the antibiotics are discharged through conduit 9, while the entrainer is conveyed to reservoir 13 through conduit 15. In most cases the antibiotics have sufficient purity and are merely dried further and sterilized. From the separator 8, the antibiotic-free extraction agent is returned to pump 10 which compresses it and conveys it to heat exchanger 11, where it is brought to the extraction tempeature. *The extraction agent is then conveyed into the base of high pressure column 4. Extraction agent losses are replenished from reservoir tank 12. The entrainers to be added to the extraction agent are obtained from reservoir tank 13. The extraction residue is taken from high pressure column 4 through conduit 16. This is the extracted solution free of antibiotics or poor in antibiotics which may still contain remainders of entrainer.

*In case of using entrainers the extraction agent from separator 8 is antibiotic-free but contains a part of the entrainer. The other part of the entrainer is recovered in stage 14, by evaporating under reduced pressure.

Several antibiotics have been isolated in pure form according to the process of the present invention from different compositions of antibiotic containing solutions.

EXAMPLE 1

An unpurified solution containing 72.2% ethanol, 23.8% water and 4% penicillin V acid (=phenoxyethyl penicillin acid) and small quantities of impurities which could only be detected by a HPLC-peak, is continuously extracted with carbon dioxide at 200 bar and 37° C. In this process, 1 liter of gas phase takes up 6 g penicillin V acid and additionally dissolves ethanol and water corresponding to the thermodynamic equilibrium conditions. The penicillin V acid is obtained from the extraction agent by expansion to 60 bar at 28° C. A high pressure liquid chromatographic (HPLC) analysis shows that the isolated penicillin V acid is extremely pure, and that during the extraction the accompanying substances present in the antibiotic containing solution almost quantitatively remain in the extraction residue.

EXAMPLE 2

An unpurified solution containing 42.5% ethanol, 40.5% water and 17% penicillin V acid (see Example 1) is extracted continuously with carbon dioxide at 200 bar and 37° C. During the extraction, 1 liter gas phase takes up 3.5 g penicillin V acid and additionally dissolves ethanol and water corresponding to the thermodynamic equilibrium conditions. From the extraction agent, the penicillin V acid is separated by expansion to 60 bar at 28° C. The product obtained is very pure and is free of the accompanying substances present in the starting solution, as proved by way of an HPLC analysis.

EXAMPLE 3

An unpurified solution containing 65% ethanol, 33.5% water and 1.5% penicillin V acid (see Example 1) is continuously extracted with ethane at 200 bar and 37° C. During the extraction, 0.9 g penicillin V are extracted by 1 liter gas phase and additionally the extraction agent takes up ethanol as well as water corresponding to the thermodynamic equilibrium conditions. The penicillin V acid is separated from the extraction agent by expansion to 40 bar at 28° C. The product is very pure and is substantially free of the accompanying substances present in the starting solution as proved by way of an HPLC analysis.

EXAMPLE 4

An unpurified solution containing 99% water, 0.6% ethyl acetate and 0.4% penicillin V acid (see Example 1) is continuously extracted with carbon dioxide at 300 bar and 37° C. During the extraction, 1 liter gas phase takes up 1.2 g penicillin V acid and additionally water and ethyl acetate are dissolved according to thermodynamic equilibrium conditions. The penicillin V acid is separated from the extraction agent by expansion to 60 bar at 28° C. The thus obtained product is very pure and the accompanying substances present in the starting solution remain almost quantitatively in the extraction residue as proved by an HPLC analysis.

EXAMPLE 5

An unpurified solution containing 93.2% ethanol, 4% water and 2.8% pleuromulin (see Example 1) is continuously extracted with ethane at 200 bar and 37° C. During the extraction, 1 liter gas phase takes up 8 g pleuromulin as well as water and ethanol corresponding to thermodynamic equilibriums. The pleuromulin is separated from the extraction agent by expansion to 40 bar at 28° C. The thus obtained end product is very pure

EXAMPLE 6

An unpurified solution containing 75.4% ethanol, 23.4% water and 1.2% griseofulvine (see Example 1) is continuously extracted with ethane at 200 bar and 37° C. During the extraction, 1 liter gas phase takes up 0.3 g griseofulvin and additionally, corresponding to thermodynamic equilibirums, water as well as ethanol. The griseofulvin is separated from the extraction agent by expansion to 40 bar at 28° C. The end product is very pure as proved by an HPLC analysis.

EXAMPLE 7

An unpurified solution containing 65% ethanol, 33.5% $H_2O$ and 1.5% penicillin V acid and small quantities of impurities, which could only be detected by a HPLC-peak, is continuously extracted with $CHClF_2$ at 200 bar and 37° C. During the extraction, 1.1 g penicillin V are extracted by 1 liter gas phase and additionally the extraction agent takes up ethanol as well as water corresponding to the thermodynamic equilibrium conditions. The penicillin V acid is separated from the extraction agent by expansion to 7 bar at 28° C. The product is very pure and is substantially free of the accompanying substances present in the starting solution as proved by way of an HPLC analysis.

EXAMPLE 8

An unpurified solution containing 93.2% ethanol, 4% $H_2O$ and 2.8% pleuromulin and small quantities of impurities, which could only be detected by a HPLC-peak, is continuously extracted with $CH_3Cl$ at 150 bar and 37° C. During the extraction, 1.5 g of pleuromulin are extracted by 1 liter gas phase and additionally the extraction agent takes up ethanol as well as water corresponding to the thermodynamic equilibrium conditions. The pleuromulin is separated from the extraction agent by expansion to 4 bar at 28° C. The product is very pure and is substantially free of the accompanying substances present in the starting solution as proved by way of an HPLC analysis.

The percentages stated in the above Examples are weight percentages.

It will be understood that the above described embodiments are for illustration only, and the present invention is susceptible to various modifications, changes and adaptations which are intended to be comprehended within the meaning and range of equivalents of the following claims.

We claim:

1. Process for isolating and purifying antibiotics selected from the group consisting of penicillins, cephalosporins, tetracyclins, aminoglucoside antibiotics, nucleoside antibiotics, macrolide antibiotics, ansamycines, and peptide antibiotics, wherein the antibiotics do not decompose during the process, comprising extracting the antibiotics from an antibiotic containing solution by contacting the solution with an extraction agent at a temperature of from 0° to 40° C. and at a pressure between the critical pressure and the ten-fold value of the critical pressure of said extraction agent, with the weight ratio of the antibiotic containing solution to the extraction agent being 1:5 to 1:20, wherein said extraction agent has a critical temperature in the range of from 0° to 160° C., is inert to the antibiotics, and precipitates the extracted antibiotics on the reduction of pressure; separating the antibiotic containing extraction agent from the extracted solution; and precipitating the antibiotics from the antibiotic containing extraction agent by lowering the pressure on the extraction agent to reduce its density, whereby essentially pure antibiotics are obtained directly without using additional precipitating agents.

2. The process of claim 1, wherein the extraction agent is returned to the extraction process step after precipitating the antibiotics.

3. The process as defined in claim 1, wherein the extraction agent is at a temperature below its critical temperature during the extraction process step.

4. Process for isolating and purifying antibiotics selected from the group consisting of penicillins, cephalosporins, tetracyclins, aminoglucoside antibiotics, nucleoside antibiotics, macrolide antibiotics, ansamycines, and peptide antibiotics, wherein the antibiotics do not decompose during the process, comprising extracting the antibiotics from an antibiotic containing solution by contacting the solution with an extraction agent, said extraction agent having a critical temperature in the range of from 0° C. to 160° C., at a temperature of from 0° to 40° C. and at a pressure between the critical pressure and the ten-fold value of the critical pressure of said extraction agent, with the weight ratio of the antibiotic containing solution to the extraction agent being 1:5 to 1:20; separating the antibiotic containing extraction agent from the extracted solution, and precipitating the antibiotics from the antibiotic containing extraction agent by reducing its density, whereby essentially pure antibiotics are obtained directly without using additional precipitating agents, wherein the extraction agent is selected from the group consisting of $CO_2$, $C_2H_4$, $C_2H_6$, $C_3H_6$, $C_3H_8$, $C_4H_{10}$, $SF_6$, $CHClF_2$, $CF_3Cl$, $CF_3Br$, $CH_3Cl$, $C_2F_2Cl_2H_2$, $N_2O$, and a mixture of two or more of these substances.

5. The process as defined in claim 1, wherein 1 to 50 weight percent of an entrainer selected from the group consisting of ethanol, methyl acetate, ethyl acetate, propyl acetate, butyl acetate, diethyl ether, acetone, methylene chloride, water, and a mixture of one or more of said compounds with water is added to the extraction agent.

6. The process as defined in claim 3, wherein the extraction agent is one or more compounds selected from the group consisting of $C_3H_6$, $C_3H_8$, $C_4H_{10}$, $SF_6$, $C_2F_2Cl_2H_2$, $CHClF_2$, $CH_3Cl$ and $CF_3Br$.

7. The process as defined in claim 4, wherein 1 to 50 weight percent of an entrainer selected from the group consisting of ethanol, methyl acetate, ethyl acetate, propyl acetate, butyl acetate, diethyl ether, acetone, methylene chloride, water, and a mixture of one or more of said compounds with water is added to the extraction agent.

* * * * *